United States Patent
Norman et al.

(10) Patent No.: US 10,976,303 B2
(45) Date of Patent: Apr. 13, 2021

(54) TEST ELEMENT RETENTION DIVIDERS

(71) Applicant: Roche Diabetes Care, Inc., Indianapolis, IN (US)

(72) Inventors: Isaac A. Norman, Indianapolis, IN (US); Frank A. Chan, Sunnyvale, CA (US)

(73) Assignee: Roche Diabetes Care, Inc., Indianapolis, IN (US)

(*) Notice: Subject to any disclaimer, the term of this patent is extended or adjusted under 35 U.S.C. 154(b) by 68 days.

(21) Appl. No.: 16/060,012

(22) PCT Filed: Dec. 7, 2016

(86) PCT No.: PCT/US2016/065462
§ 371 (c)(1),
(2) Date: Jun. 6, 2018

(87) PCT Pub. No.: WO2017/100375
PCT Pub. Date: Jun. 15, 2017

(65) Prior Publication Data
US 2018/0356390 A1    Dec. 13, 2018

Related U.S. Application Data

(60) Provisional application No. 62/264,351, filed on Dec. 8, 2015.

(51) Int. Cl.
| | |
|---|---|
| *G01N 33/487* | (2006.01) |
| *B01L 3/00* | (2006.01) |
| *B65D 25/10* | (2006.01) |
| *B01L 9/00* | (2006.01) |

(52) U.S. Cl.
CPC ........ *G01N 33/48778* (2013.01); *B01L 3/508* (2013.01); *B01L 9/52* (2013.01); *B65D 25/107* (2013.01)

(58) Field of Classification Search
CPC ..... G01N 33/48778; B01L 3/508; B01L 9/52; B65D 25/10; B65D 25/101; B65D 25/103; B65D 25/107
See application file for complete search history.

(56) References Cited

U.S. PATENT DOCUMENTS

| | | | | |
|---|---|---|---|---|
| 5,072,904 A | * | 12/1991 | Taylor | A46B 17/00 211/65 |
| 5,788,064 A | | 8/1998 | Sacherer | |
| 6,629,616 B1 | * | 10/2003 | Heinzle | A47B 47/00 211/85.7 |

(Continued)

FOREIGN PATENT DOCUMENTS

WO    2015187551    6/2015

OTHER PUBLICATIONS

International Search Report and Written Opinion for PCT/US2016/065462 dated Feb. 7, 2017, 12 pages.

*Primary Examiner* — Justin N Olamit
(74) *Attorney, Agent, or Firm* — Quarles & Brady LLP

(57) ABSTRACT

A resealable container including a housing, a lid coupled to the housing, and a basket received within the housing and including side walls defining an interior space, and a retainer extending over at least a portion of the interior space and configured to support at least one test element in at least one of a side-to-side direction and a front-to-back direction within the basket.

15 Claims, 5 Drawing Sheets

(56) References Cited

U.S. PATENT DOCUMENTS

| | | | |
|---|---|---|---|
| 7,516,845 B2* | 4/2009 | Lang | A61B 50/3001 |
| | | | 206/438 |
| 8,256,618 B2* | 9/2012 | Schein | B25H 3/06 |
| | | | 206/372 |
| 8,394,343 B2 | 3/2013 | Chan | |
| D698,459 S | 1/2014 | Chan | |
| 8,844,725 B2* | 9/2014 | Chan | B65D 25/102 |
| | | | 206/569 |
| 9,416,804 B2* | 8/2016 | Simakis | F16B 2/22 |
| 9,914,126 B2 | 3/2018 | Chan | |
| 2011/0127269 A1 | 6/2011 | Bucholtz | |
| 2013/0134159 A1* | 5/2013 | Chan | B01L 3/508 |
| | | | 220/23.83 |

* cited by examiner

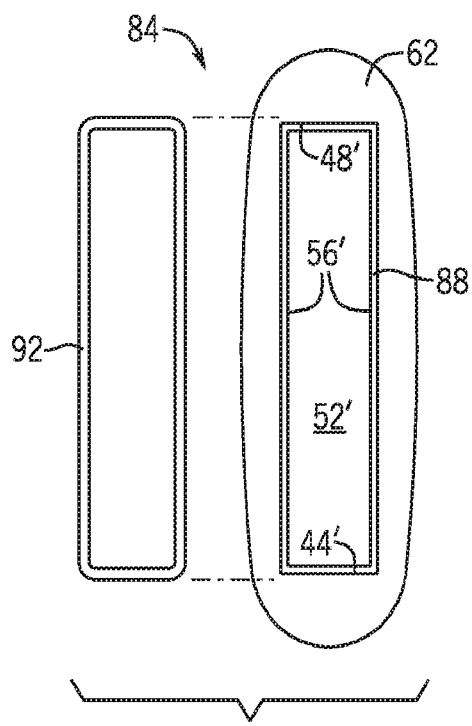
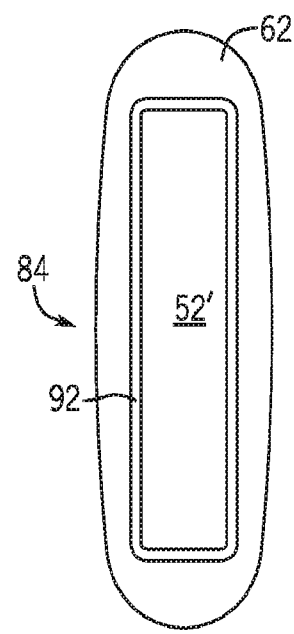
FIG. 7
FIG. 8
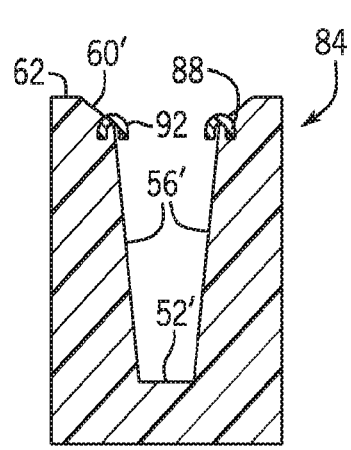
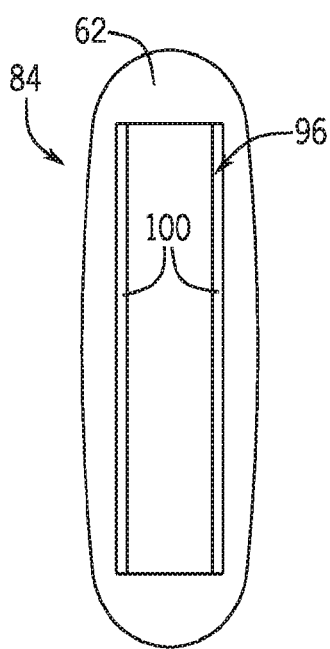
FIG. 9
FIG. 10

TEST ELEMENT RETENTION DIVIDERS

CROSS-REFERENCE TO RELATED APPLICATIONS

This application represents the national stage entry of PCT/US2016/065462, filed Dec. 7, 2016, which claims benefit of U.S. Provisional Patent Application 62/264,351 filed Dec. 8, 2015. The contents of this application are hereby incorporated by reference as set forth in their entirety herein.

TECHNICAL FIELD

The present disclosure relates generally to test element retention systems that keep test elements, such as test strips, from falling over as they are removed from a primary assist container. The present disclosure also provides systems and methods that improve the manufacturing of the products including test elements.

BACKGROUND

Containers can be used, for example, to house test elements, pills, capsules, particulate materials, liquids, or other objects or materials and control the ingress and/or egress of moisture.

Prior art systems fail to support a variety of test elements when a number of test elements are removed or a non-standard number of test elements are placed in the container. In these prior art systems, multiple test element retainers (baskets) are needed to support different test element configurations in the container. Additionally, prior art systems fail to provide a single retainer that can be used with a wide variety of test elements.

A system and method are needed that will allow a user to use a single retainer to hold a number of different test elements or other diagnostic materials, improve the ability to insert test elements into containers, and maintain the test elements in an upright and conveniently graspable position.

U.S. patent application Ser. No. 12/992,749, filed May 15, 2009, U.S. Patent Application Publication No. 2011/0127269, titled "Vial with non-round seal", Intl Patent Application No. PCT/US2015/033521, titled "Interchangeable Test Element Retainers"; U.S. Patent Application Publication No. 2013/0134159, titled "Storage Container for Biosensor Test Elements"; and U.S. Pat. No. D698,459, titled "Container" provide relevant background to the disclosure

BRIEF SUMMARY

The present disclosure provides a container. The container may be moisture-tight, and resealable. The container may include a housing, a lid coupled to the housing, and a basket received within the housing and including side walls defining an interior space. The container may also include a retainer extending over at least a portion of the interior opening. The retainer may be configured to support a test element in at least one of a side-to-side direction or a front-to-back direction within the retainer.

BRIEF DESCRIPTION OF THE DRAWINGS

The disclosure is further elucidated in the following on the basis of an exemplary configuration shown in the drawings.

FIG. 7 is a top view of the basket of FIG. 6 with a retainer removed.
FIG. 8 is a top view of the basket of FIG. 6 with the retainer in place.
FIG. 9 is a section view of the basket of FIG. 6 taken along the line 9-9 of FIG. 6.
FIG. 10 is a top view of the basket of FIG. 6 showing an alternative retainer.

Corresponding reference characters indicate corresponding parts throughout the several views of the drawing.

Figure 1:
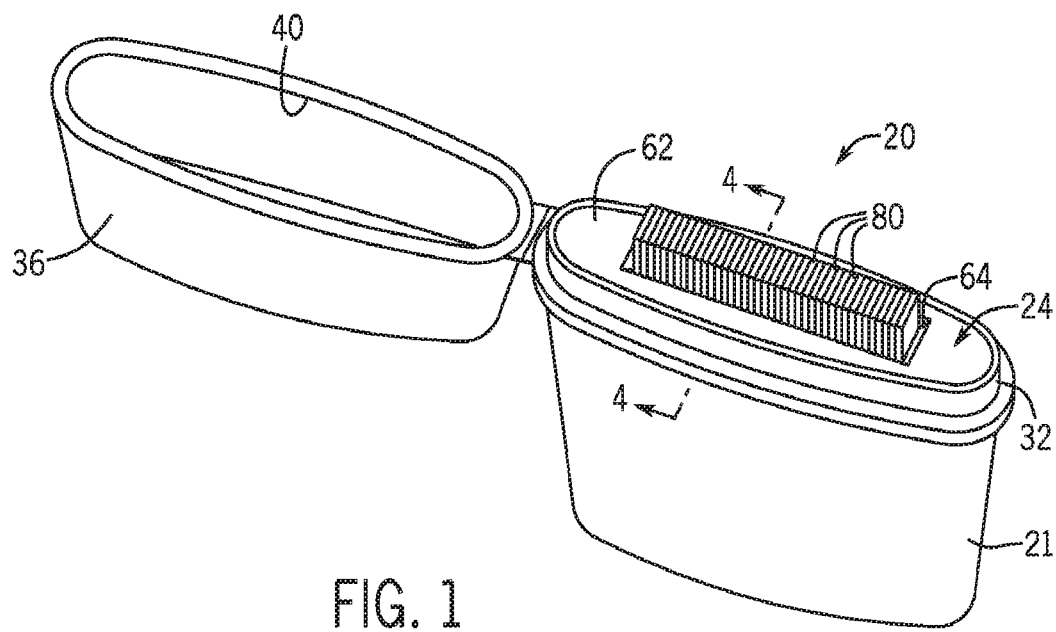
FIG. 1 is a pictorial view of a container with a cap in an open position.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

The following reference characters are used in the Figures.

| Ref. Char. | Description |
|---|---|
| 20 | Container |
| 21 | Housing |
| 24 | Basket |
| 28 | Interior space |
| 32 | Body sealing surface |
| 36 | Lid |
| 40 | Lid sealing surface |
| 44 | First end wall |
| 48 | Second end wall |
| 52 | Floor |
| 56 | Side walls |
| 60 | Recess |
| 62 | Top surface |
| 64 | Retainer |

-continued

| Ref. Char. | Description |
|---|---|
| 68 | Fingers |
| 72 | Parting line |
| 76 | End springs |
| 80 | Test elements |
| 84 | Basket |
| 88 | Channel |
| 92 | Retainer |
| 96 | Retainer |
| 100 | Side segments |
| 104 | Basket |
| 108 | Channels |
| 112 | End springs |
| 116 | Mounting portion |
| 120 | Living spring portion |
| 124 | Pressing portion |
| 128 | Retainer |
| 132 | Wiper |
| 132a | First segment |
| 132b | Second segment |
| 132c | Third segment |
| 132d | Fourth segment |
| 136 | Retainer |

DETAILED DESCRIPTION

For the purposes of promoting an understanding of the principles of the disclosure, reference will now be made to the configuration illustrated in the drawings, and specific language will be used to describe that configuration. It will nevertheless be understood that no limitation of the scope of the disclosure is intended. Alterations and modifications in the illustrated device, and further applications of the principles of the disclosure as illustrated therein, as would normally occur to one skilled in the art to which the disclosure relates are contemplated, are desired to be protected. Such alternative configurations require certain adaptations to the configurations discussed herein that would be understood by those skilled in the art.

Although specific terms are employed herein, they are used in a generic and descriptive sense only and not for purposes of limitation.

Moreover, and unless defined otherwise, all technical and scientific terms used herein have the same meaning as commonly understood by one of skill in the art to which the disclosure pertains. Although any methods and materials similar to or equivalent to those described herein can be used in the practice or testing of the retainers, systems and methods, the preferred methods and materials are described herein.

Furthermore, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B," and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

The storage containers and inserts/basket provided herein are useful in a variety of applications. For example, the containers and baskets can be used to hold a plurality of vertically oriented test elements. Because the baskets include retention dividers to frictionally engage a surface of, for example, a test element, they can be readily removed when no test elements remain. Advantageously, the baskets can be used to engage same or different numbers of test elements, as well as the same or different sized/shaped test elements within the same basket.

Test Element Retention Dividers and Baskets for Containers Including the Same

Figure 2:
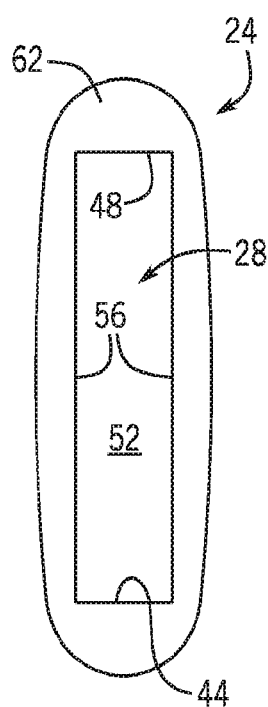
FIG. 2 is a top view of a basket removed from the container of FIG. 1 with a retainer removed.

FIG. 1 shows a vial or container 20 that includes a housing 21, a body or basket 24 with an interior space 28, a body sealing surface 32, a lid 36, and a lid sealing surface 40. A desiccant material may be arranged to communicate with the interior space 28. With reference to FIG. 2, the interior space 28 of the basket 24 is defined by a first end wall 44, a second end wall 48, and a floor 52 and side walls 56 that extend between the first end wall 44 and the second end wall 48. A recess 60 is formed in a top surface 62 of the basket 24.

Figure 3:
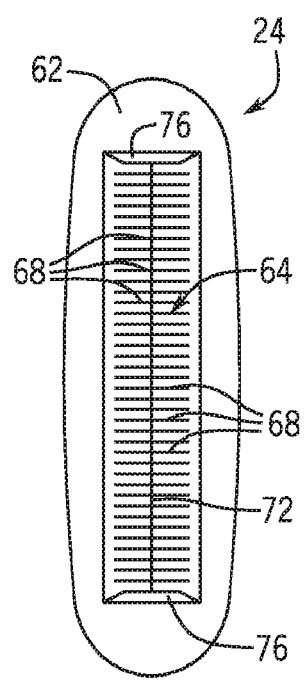
FIG. 3 is a top view of the basket of FIG. 2 with the retainer in place.

FIG. 3 shows a membrane or retainer 64 engaged with the recess 60 of the basket 24. The retainer 64 includes a plurality of segments or fingers 68 arranged on opposing sides of a parting line 72. End springs 76 may be arranged adjacent to the first end wall 44 and the second end wall 48.

The exemplary retainer 64 shown in FIG. 3 is formed with a single basket 24 and the fingers 68, parting line 72, and end springs 76, which may be cut by a die, a laser, or other suitable processes. In the illustrated non-limiting example, the retainer 64 is shaped to engage the recess 60 and hold securely in place. In one configuration, the retainer 64 is held in the recess 60 by a press fit arrangement. In other configurations, adhesive may be used. In still other configurations, the retainer 64 may be held within the recess 60 by a spring clip or other physical features of the basket 24. The retainer 64 may be formed of flexible plastic, flexible rubber, or thin metal, for example.

Figure 4:
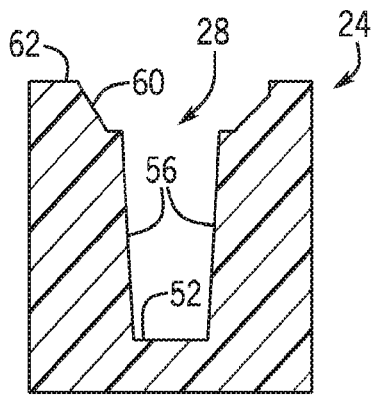
FIG. 4 is a section view of the basket of FIG. 2 taken along the line 4-4 of FIG. 1.
Figure 5:
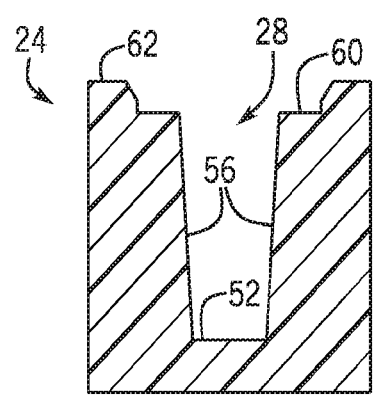
FIG. 5 is an alternative section view showing another basket that is similar to the basket of FIG. 2.

FIGS. 4 and 5 show alternative profiles for the interior space 28 of the insert 24. In the configurations of FIGS. 4 and 5, the floor 52 defines a width of about five millimetres (5 mm), the maximum width between the side walls 56 is about seven millimetres (7 mm), and the maximum width of the recess 60 is about eight millimetres (8 mm). The dimensions recited in connection with this embodiment, however, are not intended to be limiting, as one of skill in the art is capable of adapting the dimension to a particular object to be retained. The recess 60 shown in FIG. 4 is relatively deeper and defines a relatively larger oblique face, whereas the recess 60 shown in FIG. 5 has a relatively smaller oblique face and a relatively larger shoulder adjacent the side walls 56.

As used herein, "about" means within a statistically meaningful range of a value or values including, but not limited to, a stated concentration, length, width, height, angle, weight, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

In operation, test elements 80 may be loaded into the container 20 by pushing the test elements 80 past the fingers 68 such that the fingers 68 deflect inward toward the interior space 28 until the test elements 80 contact one of the side walls 56 and the floor 52. With the test elements 80 inserted into the container 20, the fingers 68 exert a force on the sides of the test elements 80 to hold the test elements 80 upright. Additionally, because the fingers 68 are separated, the fingers 68 that are not in contact with the test elements 80 are not deflected and continue to extend toward the parting line 72. The still-extended fingers 68 provide front-to-back support for the test elements 80 in the direction between the first end wall 44 and the second end wall 48. Additionally, should test elements 80 be inserted into the container 20 adjacent one of the first end wall 44 and the second end wall 48, the end springs 76 provide a front-to-back force to maintain the test elements 80 upright. The combination of the side-to-side loading by the fingers 68 and the front-to-back support by the fingers 68 and/or end springs 76 hold or maintain the test elements 80 in an upright position such that they are easily graspable or engaged by a machine.

For example, a user may insert twenty test elements 80 into the container 20. The test element 80 adjacent the first end wall 44 is supported by the fingers 68 adjacent that test element 80 and the end spring 76, while the test element 80 closest to the second end wall 48 is supported side-to-side by the adjacent fingers 68 and front-to-back by the fingers immediately toward the second end wall 48. As test elements 80 are removed from the side closest to the second end wall 48, more fingers 68 will return from the deflected position to support the remaining test elements 80. In this way, the series of test elements 80 that remains in the container 20 are always supported both side-to-side and front-to-back. Additionally, the fingers 68 and end springs 76 allow for test element 80 of different widths and thicknesses without any modification.

Figure 6:
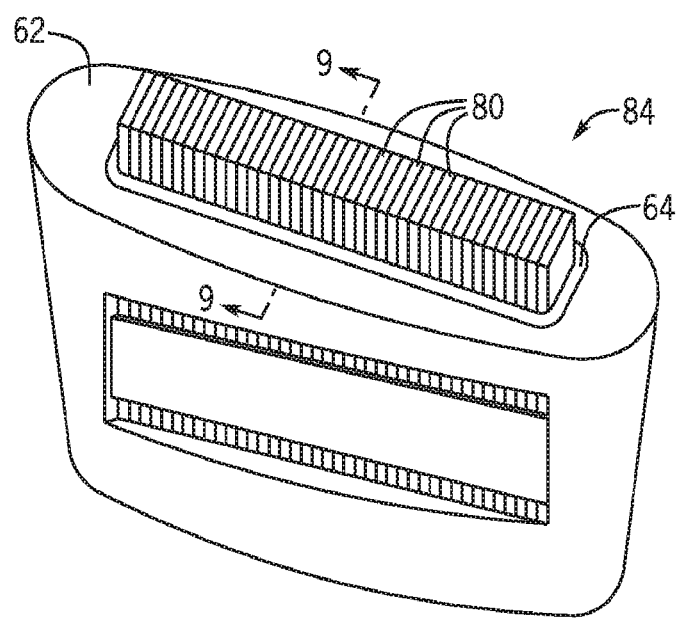
FIG. 6 is a pictorial view of another basket.

Turning to FIG. 6, another basket 84 is shown that is substantially similar to the basket 24 discussed above and marked with similar reference numerals in the single prime series. With reference to FIG. 7, the basket 84 includes a floor 52' that defines a width of about five millimetres (5 mm), a maximum width between side walls 56' of about six and one-half millimetres (6.5 mm), and a maximum width of a recess 60' is about eight millimetres (8 mm). The dimensions recited in connection with this embodiment, however, are not intended to be limiting, as one of skill in the art is capable of adapting the dimension to a particular object to be retained. The recess 60' is defined by an oblique wall and a channel 88 positioned substantially adjacent the side walls 56'. Notably, these measurements are examples and not limiting.

FIG. 8 shows a membrane or retainer 92 engaged with the channel 88. The retainer 92 is an annular member formed of flexible plastic, flexible rubber, or thin metal, for example. The retainer 92 defines a substantially inverted U-shape, cross-sectional profile (see FIG. 9). In some configurations, the retainer 92 include slits cut into the U-shaped cross sectional profile such that fingers or segments are formed that act similarly to the fingers 68 discussed above. The portions of the retainer 92 arranged along the side walls 56' provide side-to-side support for test elements 80 and the portions arranged along the first end wall 44' and the second end wall 48' provide front-to-back support for the test elements 80. The retainer 92, whether including slits/cuts or not, is able to deflect in such a way that the portions of the retainer 92 adjacent the last test element 80 in a series of test elements 80 is able to provide support in the front-to-back direction. In this way, the retainer 92 functions support test elements 80 in side-to-side and front-to-back directions.

FIG. 10 shows another retainer 96 that can be used with the basket 84 discussed above. The retainer 96 is substantially similar to the retainer 92 discussed above except that instead of being an annular retainer, the retainer 96 is formed of two substantially linear side segments 100 that are not connected. Correspondingly, the retainer 92 does not provide end springs and all front-to-back support is provided by the side segments 100 whether including slits/cuts or not.

Figure 11:
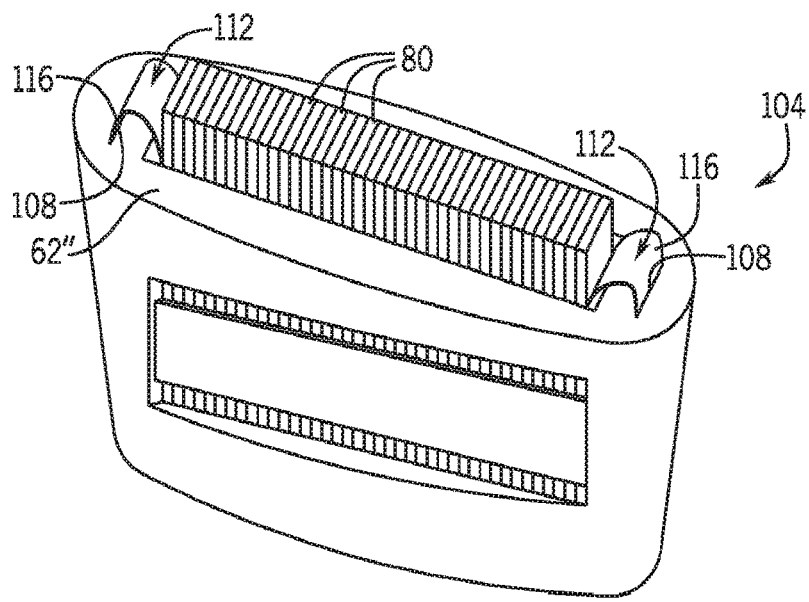
FIG. 11 is a pictorial view of another basket.
Figure 12:
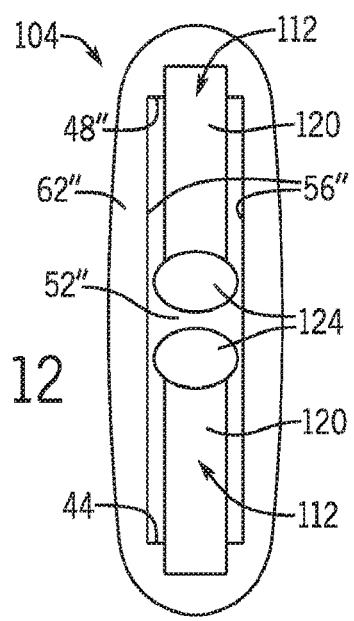
FIG. 12 is a top view of the basket of FIG. 11 with the retainer in place.
Figure 13:
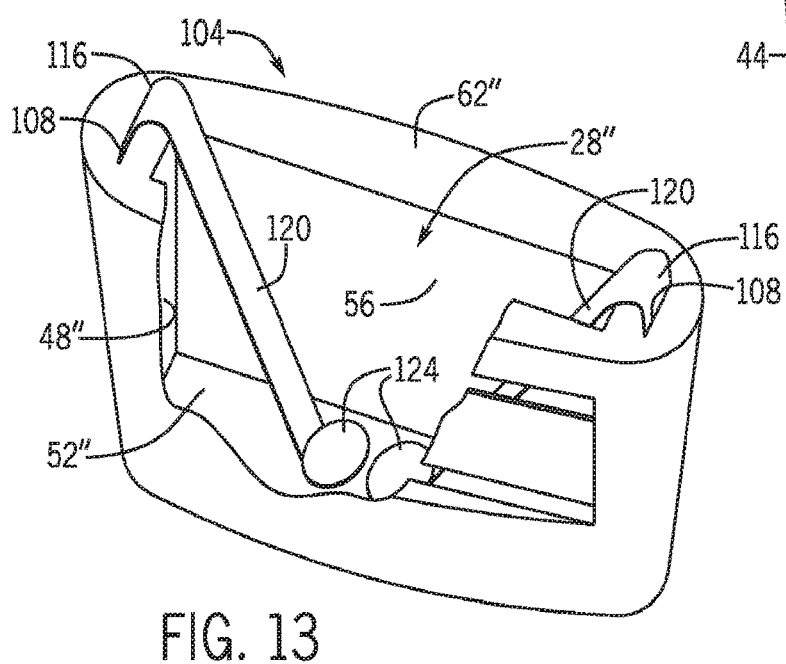
FIG. 13 is a cutaway view of the basket of FIG. 11.

FIGS. 11 and 13 show another basket 104 that is substantially similar to the basket 24 discussed above and marked with similar reference numerals in the double prime series. The basket 104 includes channels 108 cut into the top surface 62" adjacent the first end wall 44" and the second end wall 48". End springs 112 are engaged with the channels 108 and include a mounting portion 116 sized to be press fit into one of the channels 108, a living spring portion 120, and a pressing portion 124 arranged to press against test elements 80. The illustrated mounting portions 116 and living spring portions 120 may be about four millimeters (4 mm) wide and the living spring portions 120 may be sized such that in a fully extended position (see FIG. 12) the pressing portions 124 meet in a central area of the interior space 28".

In operation, the end springs 112 provide substantially no side-to-side support to test elements 80. Rather, the end springs hold the test elements 80 upright via front-to-back support only. In some configurations, the end springs 112 may be combined with other retainers as discussed above. For example, the retainer 96 and the end springs 112 may be combined effectively.

Figure 14:
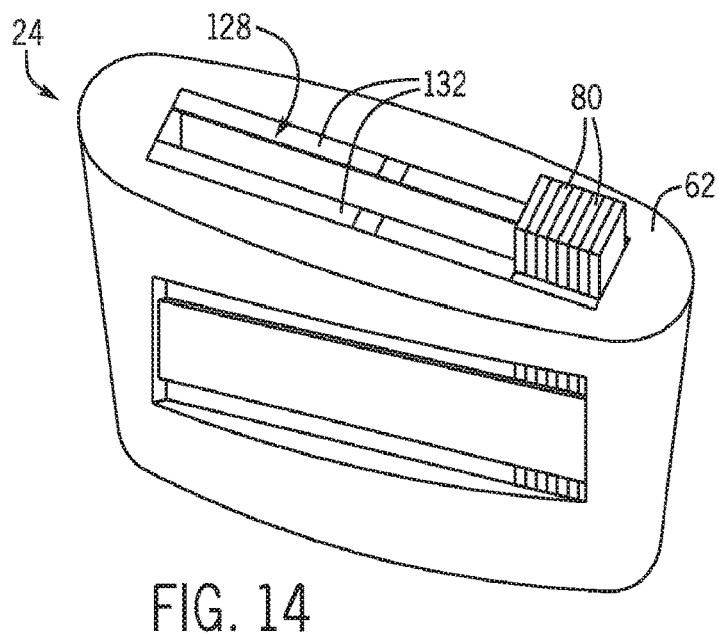
FIG. 14 is a pictorial view of another basket.
Figure 15:
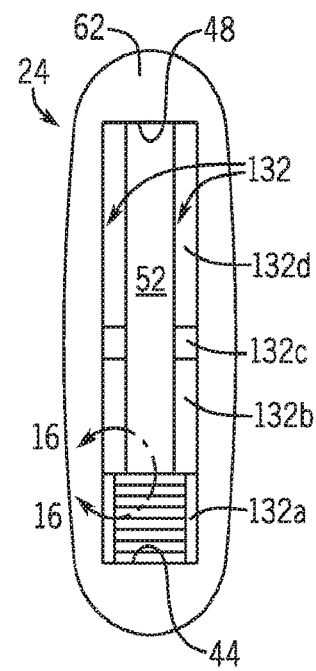
FIG. 15 is a top view of the basket of FIG. 14 with a retainer in place.
Figure 16:
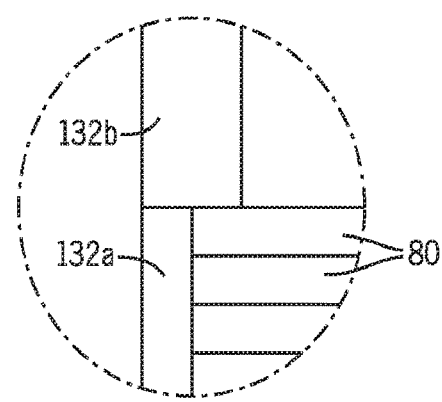
FIG. 16 is a detail view of the basket of FIG. 14 taken within the circle 16-16 of FIG. 15.

FIGS. 14-16 show a retainer 128 engaged with the basket 24 as discussed above. The retainer 128 includes, for example, two wipers 132, each divided into four segments such as a first segment 132a, a second segment 132b, a third segment 132c, and a fourth segment 132d. For example, the four segments are sized to correspond to ten test elements 80 in the first segment 132a adjacent the first end wall 44, fifteen test elements 80 in the second segment 132b, five test elements 80 in the third segment 132c, and fifteen to twenty test elements 80 in the fourth segment 132d adjacent the second end wall 48. It is contemplated, however, that the retainer 128 can include a single wiper that is long enough to cover the distance of the opening. In either instance, however, and similar to the other retainers discussed above, sections of unused wiper 132 sections act as backers to provide support to the remaining test elements 80. FIG. 16 shows a detail of how the unused second segment 132b of the wiper 132 provides front-to-back support to the remaining test elements 80. In other configurations, the sections may be spaced or sized differently. In addition, the wiper 132 may extend farther across the interior space 28 or may extend less far across the interior space 28, as desired.

Figure 17:
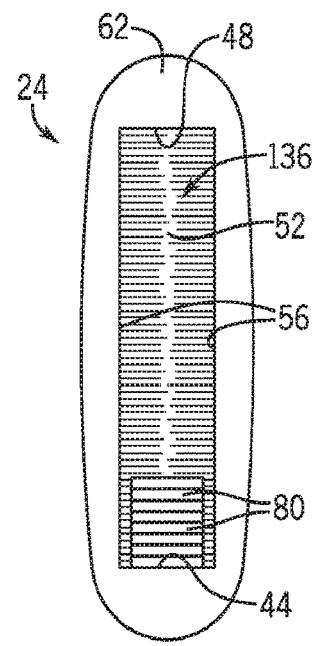
FIG. 17 is a top view of another basket with a retainer in place.

FIG. 17 shows a retainer 136 that includes a plurality of bristles that are each individually deflectable by the test elements 80. The bristles are arranged to deflect or bend down into the interior space 28 as a test element 80 is inserted into the container 20 and pop back up when the test element 80 is removed. The bristles also provide front-to-back support for about one to about fifty test elements 80.

Any aspects of the above configurations may be combined to arrive at combinations that can be useful and are contemplated within the scope of this disclosure.

Aspects of the disclosure provide a single basket insert that allows for multiple configurations (e.g., strip counts) of test elements or strips to be placed in the container. Also, aspects of the disclosure maintain test elements or strips upright in containers even as other strips are pulled out. The test element or strip retention retainers or dividers will allow machines to quickly switch between configurations, by allowing operations to use the same container. Strip retention with supportive backing allows for multiple test strip configurations to be inserted in the container. As test strips are removed, the remaining strips are supported by a flexible side/back membrane or retainer. Retention of test strips is provided without allowing the test strips to fall over within the container. The retainer segments can be made in different increment values (e.g. the thickness of less than 1 strip or up to the length of the container opening), as desired. The retainer segments can be divided equal distances from the side walls or can be varied in length from the side walls (offset). The retainer segment top profile can be (but is not limited to) rounded, square, or angled. The retainer segment sides and leading edge profile can be (but are not limited to) rounded, square, or angled. The color of the retainer or divider can be any color that is appropriate for the material be used, or to aid in the manufacturing process. The retainer segments can be tightly sealed together or open to allow for air flow. The retainer segments can be perforated or fully cut through. The length of the retainer segments can be overlapping to allow for more engagement of the test strips.

Although configurations of the disclosure have been described using specific terms, such description is for illustrative purposes only, and it is to be understood that changes and variations obvious to one of skill in the art are to be considered within the scope of the claims that follow and their equivalents. All of the patents, patent applications, patent application publications and other publications recited herein are hereby incorporated by reference as if set forth in their entirety.

The present inventive concept has been described in connection with what are presently considered to be the most practical and preferred configurations. However, the inventive concept has been presented by way of illustration and is not intended to be limited to the disclosed configurations. Accordingly, one of skill in the art will realize that the inventive concept is intended to encompass all modifications and alternative arrangements within the spirit and scope of the inventive concept as set forth in the appended claims.

Numbered Configurations

In addition or as an alternative to the above, the following configurations are described 1. A resealable container comprising:
   a housing;
   a lid coupled to the housing; and
   a basket received within the housing and including side walls defining an interior space, and a retainer extending over at least a portion of the interior space and configured to support at least one test element in at least one of a side-to-side direction and a front-to-back direction within the basket.

2. The resealable container of Embodiment 1, wherein the retainer includes a plurality of fingers.

3. The resealable container of Embodiment 2, wherein the fingers extend to a parting line.

4 The resealable container of Embodiments 2 or 3, wherein the fingers substantially cover the entire interior space.

5. The resealable container of any one of Embodiments 2 to 4, wherein the retainer is formed as a single piece and the fingers are cut from the single piece.

6. The resealable container of any one of Embodiments 2 to 5, wherein each individual finger is configured to be deflected by the test element.

7. The resealable container of any one of Embodiments 1 to 6, wherein the retainer includes a wiper cut into a plurality of segments.

8. The resealable container of Embodiment 7, wherein each segment is configured to support a plurality of test elements.

9. The resealable container of Embodiments 7 or 8, wherein each segment is configured to be deflected by the test element.

10. The resealable container of any one of Embodiments 7 to 9, wherein an unused segment in configured to provide the front-to-back support to the test element supported by an adjacent segment.

11. The resealable container of any one of Embodiments 7 to 10, wherein the retainer includes at least four segments.

12. The resealable container of any one of Embodiments 7 to 11, wherein the wiper is configured to provide air flow to the test element.

13. The resealable container of any one of Embodiments 1 to 12, wherein the retainer includes an annular member.

14. The resealable container of any one of Embodiments 1 to 13, wherein the retainer defines a substantially inverted U-shaped cross-sectional profile.

15. The resealable container of any one of Embodiments 1 to 14, wherein the retainer includes an end spring configured to provide front-to-back support to the test element.

16 The resealable container of Embodiment 15, wherein the end spring is a living spring.

17. The resealable container of Embodiments 15 or 16, wherein the retainer is formed from a single piece and the end spring is cut from the single piece.

18. The resealable container of any one of Embodiment 1 to 17, wherein the retainer is adhered to the basket.

19 The resealable container of any one of Embodiments 1 to 18, wherein the retainer is press fit into the basket.

20. The resealable container of any one of Embodiments 1 to 19, wherein the retainer is constructed of at least one of flexible plastic, flexible bristles, flexible rubber, and thin metal.

21. A basket for use in a resealable container, the basket comprising:
   a sidewall defining and interior space; and
   a retainer including at least one segment, the segment deflectable between a first position and a second position, when in the first position the segment is configured to provide side-to-side support of a test element, and when in the second position the segment is configured to provide front-to-back support of the test element.

22. A resealable container as substantially described and shown herein.

23. A basket for use in a resealable container as substantially described and shown herein.

The disclosure claimed is:

1. A resealable container comprising:
   a housing;
   a lid coupled to the housing; and
   a basket received within the housing and including
      a first side wall and a second side wall defining an interior space, and
      a retainer extending over at least a portion of the interior space and configured to support at least one test element in a side-to-side direction and a front-to-back direction within the basket, the retainer further comprising:
- a first plurality of fingers extending from the first side wall to a parting line positioned between the first side wall and the second side wall in the interior space; and
- and second plurality of fingers extending from the second side wall to the parting line, wherein:
  - a first finger in the first plurality of fingers and a second finger in the second plurality of fingers are configured to deform in response to insertion of at least one test element into the interior space to provide side-to-side support of the at least one test element; and
  - an unused third finger in the first plurality of fingers and an unused fourth finger in the second plurality of fingers are configured to not deform in response to the insertion of the at least one test element into the interior space to provide front-to-back support to the at least one test element, wherein the first finger and the third finger are different sizes.

2. The resealable container of claim 1, wherein the retainer is formed as a single piece and the first plurality of fingers and the second plurality of fingers are cut from the single piece.

3. The resealable container of claim 1, wherein the first finger and the second finger are each formed as a bristle configured to deform and provide side-to-side support for one test element.

4. The resealable container of claim 1, wherein the first finger and the second finger are each formed as a wiper configured to deform and provide side-to-side support for a plurality of test elements.

5. The resealable Container of claim 4, wherein the wiper is configured to provide air flow to the plurality of test elements.

6. The resealable container of claim 1, wherein the first plurality of fingers and the second plurality of fingers are formed in an annular member of the retainer.

7. The resealable container of claim 1, wherein the retainer defines a substantially inverted U-shaped cross-sectional profile.

8. The resealable container of claim 1, wherein the retainer includes an end spring configured to provide front-to-back support to the at least one test element.

9. The resealable container of claim 8, wherein the end spring is a living spring.

10. The resealable container of claim 8, wherein the retainer is formed from a single piece and the end spring is cut from the single piece.

11. The resealable container of claim 1, wherein the retainer is adhered to the basket.

12. The resealable container of claim 1, wherein the retainer is press fit into the basket.

13. The resealable container of claim 1, wherein the retainer is constructed of at least one of flexible plastic, flexible bristles, flexible rubber, and thin metal.

14. The resealable container of claim 1, further comprising a floor, wherein the interior space has a trapezoidal cross-section in which the first side wall and the second side wall form two sides of the trapezoidal cross-section and the floor forms a third side of the trapezoidal cross-section.

15. A basket for use in a resealable container, the basket comprising:
- a sidewall defining an interior space; and
- a retainer including a plurality of segments, each segment in the plurality of segments being deflectable between a first position and a second position, when in the first position at least one segment in the plurality of segments is configured to provide side-to-side support of a test element that deflects the at least one segment into the first position, and when in the second position at least one other segment in the plurality of segments that does not deflect is configured to provide front-to-back support of the test element, wherein the at least one segment and the at least one other segment have different sizes.

* * * * *